US009226889B2

(12) United States Patent
Braun et al.

(10) Patent No.: US 9,226,889 B2
(45) Date of Patent: Jan. 5, 2016

(54) SILICONE ACRYLATE AND ACRYLIC ACID THICKENING POLYMER REDUCING THE STICKINESS OF GLYCERINE-BASED COSMETIC FORMULAS

(71) Applicants: Olivier Braun, St Rambert (FR); Paul Mallo, Croissy-sur-Seine (FR)

(72) Inventors: Olivier Braun, St Rambert (FR); Paul Mallo, Croissy-sur-Seine (FR)

(73) Assignee: SOCIETE D'EXPLOITATION DE PRODUITS POUR LES INDUSTRIES CHIMIQUES SEPPIC, Paris (FR)

(*) Notice: Subject to any disclaimer, the term of this patent is extended or adjusted under 35 U.S.C. 154(b) by 0 days.

(21) Appl. No.: 14/380,428

(22) PCT Filed: Feb. 18, 2013

(86) PCT No.: PCT/FR2013/050327
§ 371 (c)(1),
(2) Date: Aug. 22, 2014

(87) PCT Pub. No.: WO2013/132169
PCT Pub. Date: Sep. 12, 2013

(65) Prior Publication Data
US 2015/0011658 A1    Jan. 8, 2015

(30) Foreign Application Priority Data

Mar. 8, 2012   (FR) ...................... 12 52106

(51) Int. Cl.
| | |
|---|---|
| A61K 8/81 | (2006.01) |
| A61Q 19/00 | (2006.01) |
| C08F 220/06 | (2006.01) |
| C08F 230/08 | (2006.01) |
| A61K 8/34 | (2006.01) |
| A61K 8/893 | (2006.01) |
| C08F 283/12 | (2006.01) |
| A61Q 1/14 | (2006.01) |
| A61Q 5/00 | (2006.01) |
| A61Q 1/02 | (2006.01) |

(52) U.S. Cl.
CPC .............. *A61K 8/8152* (2013.01); *A61K 8/345* (2013.01); *A61K 8/893* (2013.01); *A61Q 1/14* (2013.01); *A61Q 19/00* (2013.01); *C08F 220/06* (2013.01); *C08F 230/08* (2013.01); *C08F 283/124* (2013.01); *A61K 2800/10* (2013.01); *A61K 2800/34* (2013.01); *A61K 2800/48* (2013.01); *A61K 2800/52* (2013.01); *A61K 2800/5424* (2013.01); *A61Q 1/02* (2013.01); *A61Q 5/00* (2013.01)

(58) Field of Classification Search
None
See application file for complete search history.

(56) References Cited

U.S. PATENT DOCUMENTS

| | | | |
|---|---|---|---|
| 5,004,598 | A | 4/1991 | Lochhead et al. |
| 5,368,850 | A | 11/1994 | Cauwet et al. |
| 5,549,681 | A | 8/1996 | Segmueller |
| 5,688,514 | A | 11/1997 | Chaudhry et al. |
| 5,804,202 | A | 9/1998 | Chaudhry et al. |
| 5,888,482 | A | 3/1999 | Amalric et al. |
| 5,928,656 | A | 7/1999 | Chaudhry et al. |
| 6,051,245 | A | 4/2000 | Chaudhry et al. |
| 6,136,305 | A | 10/2000 | Michel-Lecocu et al. |
| 6,346,239 | B1 | 2/2002 | Mallo et al. |
| 7,208,544 | B2 | 4/2007 | Kawae et al. |
| 7,270,853 | B2 | 9/2007 | Rodrigues et al. |
| 7,588,334 | B2 | 9/2009 | Matsushita et al. |
| 7,776,985 | B2 | 8/2010 | Rodrigues et al. |
| 7,829,627 | B2 | 11/2010 | Rodrigues et al. |
| 8,106,118 | B2 | 1/2012 | Rodrigues et al. |
| 8,840,870 | B2 * | 9/2014 | Tamareselvy et al. ........ 424/70.7 |
| 2003/0105228 | A1 | 6/2003 | Kawase et al. |
| 2003/0134968 | A1 * | 7/2003 | Kang et al. .................... 524/588 |
| 2004/0097652 | A1 | 5/2004 | Kawase et al. |
| 2004/0254290 | A1 | 12/2004 | Rodrigues et al. |

(Continued)

FOREIGN PATENT DOCUMENTS

| | | |
|---|---|---|
| DE | 19523596 | 1/1997 |
| EP | 0 503 853 | 9/1992 |

(Continued)

OTHER PUBLICATIONS

International Search Report dated Apr. 12, 2013, corresponding to PCT/FR2013/050327.
French Search Report dated Jul. 10, 2012, corresponding to the Foreign Priority Application No. 1252106.

*Primary Examiner* — Robert S Loewe
(74) *Attorney, Agent, or Firm* — Young & Thompson

(57) ABSTRACT

An anionic polyelectrolyte resulting from the polymerization: a) of a mass ratio greater than or equal to 80% and less than or equal to 99.5% of monomeric units from a monomer with a weak acid function; b) of a mass ratio greater than or equal to 0.5% and less than or equal to 20%, —Either of a monomer of formula (Ia): R—$(CH_2)_3$—$Si(CH_3)_2$—[O—Si$(CH_3)_2$—]$_n$O—$Si(CH_3)_2$—$(CH_2)_3$—R (Ia), wherein R represents the monovalent radical: —(O—$CH_2$—$CH_2$-)x[O—$CH_2$—$CH(CH_3)$-]yO—C(=O)—CH=$CH_2$, —Or of a monomer of formula (Ib): $Si(CH_3)_3$—[O—$Si(CH_3)_2$—]$_m$[O—$Si(CH_3)$[$(CH_2)_3$—R]—]$_p$O—$Si(CH_2)_3$ (Ib), c) optionally of a mass ratio greater than 0% and less than or equal to 5% of monomeric units from at least one monomer of formula (II): $R_2$—C(=O)—O—[($CH_2$—$CH(R_4)$—O]$_m$—$R_3$ (II), d) optionally of a mass ratio greater than 0% and less than or equal to 5% of at least one monomer with diethylenic or polyethylenic cross-linking; method for the preparation thereof and use as a thickener in topical compositions.

13 Claims, No Drawings

(56) References Cited

U.S. PATENT DOCUMENTS

| | | |
|---|---|---|
| 2007/0231354 A1* | 10/2007 | Sogabe et al. ............... 424/401 |
| 2007/0232755 A1 | 10/2007 | Matsushita et al. |
| 2008/0004416 A1 | 1/2008 | Rodrigues et al. |
| 2008/0021151 A1 | 1/2008 | Rodrigues et al. |
| 2011/0009543 A1 | 1/2011 | Rodrigues et al. |
| 2012/0237464 A1* | 9/2012 | Ahn et al. ..................... 424/59 |

FOREIGN PATENT DOCUMENTS

| | | |
|---|---|---|
| EP | 0 603 019 | 6/1994 |
| EP | 0 684 024 | 11/1995 |
| EP | 1 266 914 | 12/2002 |
| EP | 1 486 516 | 12/2004 |
| EP | 1 750 157 | 2/2007 |
| FR | 2 734 496 | 11/1996 |
| WO | 92/06778 | 4/1992 |
| WO | 92/21316 | 12/1992 |
| WO | 92/21318 | 12/1992 |
| WO | 93/07856 | 4/1993 |
| WO | 93/08204 | 4/1993 |
| WO | 94/27561 | 12/1994 |
| WO | 95/04592 | 2/1995 |
| WO | 95/13863 | 5/1995 |
| WO | 96/37285 | 11/1996 |
| WO | 98/09611 | 3/1998 |
| WO | 98/22207 | 5/1998 |
| WO | 98/47610 | 10/1998 |
| WO | 01/32727 | 5/2001 |

* cited by examiner

SILICONE ACRYLATE AND ACRYLIC ACID THICKENING POLYMER REDUCING THE STICKINESS OF GLYCERINE-BASED COSMETIC FORMULAS

A subject matter of the invention is novel thickening agents and their use in cosmetics and in pharmaceuticals.

It is well known to thicken aqueous phases intended for cosmetic, dermopharmaceutical or pharmaceutical applications by introducing therein synthetic or natural hydrophilic polymers. Natural polymers, such as xanthan or guar gums, are fairly widely used but exhibit the conventional disadvantages of natural products (fluctuating quality and price).

For this reason, synthetic thickening polymers are widely used in the cosmetics, dermopharmaceutical or pharmaceutical industry. Thickeners which operate over a broad pH range and which have the advantage of being particularly well tolerated have already been provided by several companies, including the applicant company.

Mention may in particular be made of the synthetic thickeners described in the patents U.S. Pat. Nos. 6,197,287, 6,136,305, 6,346,239 or also EP 0 503 853, or also U.S. Pat. No. 5,004,598.

These polymers are provided in the inverse latex or powder form. They are essentially intended to thicken aqueous phases comprising the various conventional constituents which can be found in topical formulations of the cosmetics, dermopharmaceutical or pharmaceutical industry. Mention will in particular be made of oils, surfactants (nonionic or anionic), also known as emulsifiers, inorganic salts or weak acids.

In point of fact, some formulations, more particularly those intended for the care of the skin, also comprise relatively high amounts of glycerol, typically between 5% and 10% by weight, in order to increase their moisturizing potential. However, as the presence of glycerol within them also considerably increases their sticky effect, preparers add silicone oils thereto in order to limit or eliminate this sticky effect.

However, the addition of silicone oils complicates the preparation of these formulations. Furthermore, the presence of silicone oils in formulations which are intended to be in direct contact with the skin is badly received by the final consumer.

The cosmetics industry is thus attempting to limit the use of them.

Today, none of the thickening polymers present on the market is satisfactory from this viewpoint.

The inventors have thus attempted to develop novel thickening polymers which are effective over a broad pH range and which are capable of reducing or eliminating the sticky effect brought about by the presence of glycerol, without it being necessary to add a third compound, such as silicone derivatives. They have found that powders of polymers resulting from the precipitating polymerization of silicone monomers and of monomers having a weak acid functional group solve these problems.

For this reason, according to a first aspect, a subject matter of the invention is a linear, branched or crosslinked anionic polyelectrolyte resulting from the polymerization, for 100% by weight:

a) of a proportion by weight of greater than or equal to 80% and less than or equal to 99.5% of monomer units resulting from a monomer comprising a weak acid functional group;

b) of a proportion by weight of greater than or equal to 0.5% and less than or equal to 20%, either of a monomer of formula (Ia):

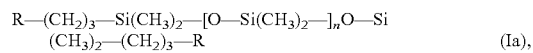

in which:
R represents the monovalent radical:

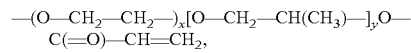

in which x and y represent, independently of one another, an integer of greater than or equal to 0 and less than or equal to 40, it being understood that the sum x+y is greater than 0 and less than 50; and n represents an integer of greater than or equal to 0 and less than or equal to 45, said monomer of formula (Ia) having a molecular weight of greater than or equal to 1500 and less than or equal to 7000;

or of a monomer of formula (Ib):

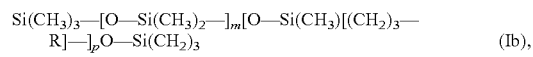

in which:
R represents a monovalent radical of formula:

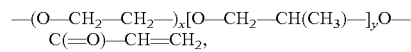

in which x and y represent, independently of one another, an integer of greater than or equal to 0 and less than or equal to 40, it being understood that the sum x+y is greater than 0 and less than 50;

m represents an integer of greater than or equal to 1 and less than or equal to 7, and p represents, independently of m, an integer of greater than or equal to 1 and less than 20;

said monomer of formula (Ib) having a molecular weight of greater than or equal to 1000 and less than or equal to 4000;

c) optionally of a proportion by weight of greater than 0% and less than or equal to 5% of monomer units resulting from at least one monomer of formula (II):

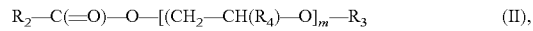

in which formula (II) m represents a number greater than or equal to 0 and less than or equal to 50, $R_2$ represents an unsaturated monovalent aliphatic radical comprising from 2 to 4 carbon atoms, $R_4$ represents a hydrogen atom, a methyl radical or an ethyl radical and $R_3$ represents a saturated or unsaturated, linear or branched, aliphatic hydrocarbon radical comprising from 8 to 30 carbon atoms, and d) optionally of a proportion by weight of greater than 0% and less than or equal to 5% of at least one diethylenic or polyethylenic crosslinking monomer.

The term "branched polyelectrolyte" denotes a nonlinear polyelectrolyte which has pendant chains, so as to obtain, when it is dissolved in water, a high state of entanglement resulting in very high viscosities at low rate gradient.

The term "crosslinked polyelectrolyte" denotes a nonlinear polyelectrolyte which is provided in the form of a three-dimensional network which is insoluble in water but which can expand in water and which thus results in the achievement of a chemical gel.

The polyelectrolyte obtained by the process according to the invention can comprise crosslinked units and/or branched units.

The term "monomer comprising a weak acid functional group" denotes in particular the monomers chosen from acrylic acid, methacrylic acid, itaconic acid, maleic acid or 3-methyl-3-[(1-oxo-2-propenyl)amino]butanoic acid.

According to a specific aspect, the said monomer comprising a weak acid functional group is acrylic acid.

According to another specific aspect, the linear, branched or crosslinked polyelectrolyte is characterized in that the proportion by weight of monomer units resulting from the monomer comprising a weak acid functional group is less than or equal to 98%.

In the formula (II) as defined above, the divalent radical:

represents in particular:
- either a chain composed solely of ethoxyl groups ($R_4$=H; n>0),
- or a chain composed solely of propoxyl groups ($R_4$=$CH_3$; n>0),
- or a chain composed solely of butoxyl groups ($R_4$=$C_2H_5$; n>0),
- or a chain composed of at least two different groups chosen from the ethoxyl, propoxyl and/or butoxyl groups.

When this chain is composed of different groups, they are distributed all along this chain, sequentially or randomly.

The term "saturated or unsaturated, linear aliphatic hydrocarbon radical comprising from 8 to 30 carbon atoms" denotes more particularly for $R_3$, in the formula (II) as defined above:
- either a radical derived from linear primary alcohols, such as, for example, those derived from octyl, pelargonic, decyl, undecyl, undecenyl, lauryl, tridecyl, myristyl, pentadecyl, cetyl, heptadecyl, stearyl, oleyl, linoleyl, nonadecyl, arachidyl, behenyl, erucyl or 1-triacontyl alcohol. They are then the octyl, nonyl, decyl, undecyl, 10-undecenyl, dodecyl, tridecyl, tetradecyl, pentadecyl, hexadecyl, heptadecyl, octadecyl, 9-octadecenyl, 10,12-octadeca-dienyl, 13-docosenyl or triacontanyl radicals;
- or a radical derived from Guerbet alcohols, which are branched 1-alkanols corresponding to the general formula:

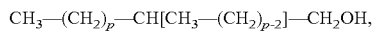

in which p represents an integer of between 2 and 14, such as, for example, the 2-ethylhexyl, 2-propylheptyl, 2-butyloctyl, 2-pentylnonyl, 2-hexyldecyl or 2-octyl-dodecyl radical;
- or a radical derived from the isoalkanols corresponding to the general formula:

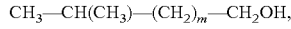

in which m represents an integer of between 2 and 26, such as, for example, the 4-methylpentyl, 5-methyl-hexyl, 6-methylheptyl, 15-methylpentadecyl or 16-methylheptadecyl radical;
- or the 2-hexyloctyl, 2-octyldecyl or 2-hexyl-dodecyl radical.

The term "saturated or unsaturated, linear or branched, aliphatic hydrocarbon radical comprising from 8 to 30 carbon atoms" more particularly denotes for $R_3$ in the formula (II) as defined above, an alkyl radical comprising from 12 to 22 carbon atoms.

In the formula (II) as defined above, m more particularly represents a number greater than or equal to 0 or less than or equal to 25.

In the formula (II) as defined above, $R_2$ more particularly represents the vinyl ($CH_2$=CH—) radical or the isopropenyl [$CH_2$=C($CH_3$)—] radical.

According to a more specific aspect of the present invention, said monomer of formula (II) as defined above is chosen from:
- pentacosaethoxylated behenyl methacrylate, the compound of formula (II) as defined above in which $R_3$ represents the docosanyl radical, $R_2$ represents the isopropenyl radical, $R_4$ represents a hydrogen atom and n is equal to 25;
- tetraethoxylated lauryl acrylate, which compound corresponds to the formula (II) as defined above in which $R_3$ represents the dodecyl radical, $R_2$ represents the vinyl radical, $R_4$ represents a hydrogen atom and n is equal to 4,
- eicosaethoxylated stearyl methacrylate, the compound of formula (II) as defined above in which $R_3$ represents the stearyl radical, $R_2$ represents the isopropenyl radical, $R_4$ represents a hydrogen atom and n is equal to 20,
- tetraethoxylated lauryl methacrylate, which compound corresponds to the formula (I) as defined above in which $R_3$ represents the dodecyl radical, $R_2$ represents the isopropenyl radical, $R_4$ represents a hydrogen atom and n is equal to 4, or
- stearyl methacrylate, the compound of formula (II) as defined above in which $R_3$ represents the stearyl radical, $R_2$ represents the isopropenyl radical, $R_4$ represents a hydrogen atom and n is equal to 0.

According to a more specific aspect of the present invention, said monomer of formula (Ia) as defined above is Silmer™ ACR Di-50, sold by Siltech, with a molecular weight equal to 4100 and referenced in Chemical Abstracts under the registry number RN=128754-61-0.

According to a more specific aspect of the present invention, said monomer of formula (Ia) as defined above is Silmer™ ACR Di-10, sold by Siltech, with a molecular weight equal to 1100.

According to a more specific aspect of the present invention, said monomer of formula (Ib) as defined above is Silmer™ ACR D208, sold by Siltech, with a molecular weight equal to 3000 and referenced in Chemical Abstracts under the registry number RN=518299-28-0.

According to a more specific aspect of the present invention, said monomer of formula (Ib) as defined above is Silmer™ ACR D2, sold by Siltech, with a molecular weight equal to 1400 and referenced in Chemical Abstracts under the registry number RN=158061-40-6.

According to a specific aspect, a subject matter of the invention is more particularly a polyelectrolyte as defined above resulting from the polymerization, for 100% by weight:
a) of a proportion by weight of greater than or equal to 85% and less than or equal to 98% of monomer units resulting from a monomer comprising a weak acid functional group;
b) of a proportion by weight of greater than or equal to 1% and less than or equal to 14% of monomer units resulting from a monomer of formula (Ia) as defined above or from a monomer of formula (Ib) as defined above; and
c) of a proportion by weight of greater than or equal to 1% and less than or equal to 5% of monomer units resulting from the compound of formula (II) as defined above.

According to another specific aspect of the present invention, the polyelectrolyte as defined above is crosslinked.

According to the latter aspect, said at least one diethylenic or polyethylenic crosslinking monomer is chosen in particular from diallyloxyacetic acid or one of the salts, such as its sodium salt, triallylamine, trimethylolpropane triacrylate, ethylene glycol dimethacrylate, diethylene glycol diacrylate, diallylurea or methylenebis(acrylamide), or a mixture of several of these compounds.

According to a very specific aspect of the present invention, the crosslinking agent employed is methylenebis(acrylamide) or trimethylolpropane triacrylate (TMPTA).

The crosslinking agent is then generally employed in the molar proportion, expressed with respect to the monomers employed, of 0.005% by weight to 5% by weight and more particularly of 0.5% by weight to 2.5% by weight.

Another subject matter of the invention is a process for the preparation of the polyelectrolyte as defined above, characterized in that it comprises:
- a stage a) of preparation of a reaction mixture comprising, in the desired molar proportions and in an organic solvent (S), the monomer or monomers comprising a weak acid functional group, the monomer of formula (Ia) or the monomer of formula (Ib); if necessary or if desired, the monomer units resulting from the compound of formula (II); and, if necessary or if desired, the diethylenic or polyethylenic crosslinking monomer or monomers,
- a stage b) during which the polymerization reaction is initiated by introduction, into said reaction mixture prepared in stage a), of a free radical initiator and is then allowed to take place until its conclusion, in order to obtain a precipitate of said polyelectrolyte.

According to another specific aspect of the present invention, in stage b) of the process as defined above, the polymerization reaction is initiated at a temperature equal to or greater than 50° C. using a radical initiator which produces radicals by homolysis, such as dilauroyl peroxide, azobis(isobutyronitrile) or also azo derivatives.

According to another specific aspect of the present invention, in stage b) of the process as defined above, the polymerization reaction is initiated by a redox pair, such as a redox pair which generates hydrogensulfite ($HSO_3$) ions, such as the cumene hydroperoxide/sodium metabisulfite ($Na_2S_2O_5$) pair or the cumene hydroperoxide/thionyl chloride ($SOCl_2$) pair, at a temperature of less than or equal to 20° C., if desired accompanied by a polymerization coinitiator, such as, for example, azobis(isobutyronitrile) or dilauroyl peroxide, and then carried out quasiadiabatically.

The process as defined above can additionally comprise:
- a stage c) of isolation of said precipitate obtained in stage b) by separation from said solvent (S) and then, if necessary or if desired,
- a stage d) of drying said precipitate resulting from stage c).

According to another specific aspect of the present invention, in stage c) of the process as defined above, the separation of the precipitate obtained from said organic solvent is carried out by filtration.

According to another specific aspect, a subject matter of the invention is a process as defined above in which said organic solvent (S) is chosen from toluene, benzene, cyclohexane, heptane, ethyl acetate, trichloromethane, dichloroethane or a mixture of the latter.

According to a more specific aspect, a subject matter of the invention is a process as defined above in which the solvent (S) is a cyclohexane/ethyl acetate mixture.

Another subject matter of the invention is the use of the anionic polyelectrolyte as defined above as thickener and/or as stabilizer and/or as emulsifier for a cosmetic, dermopharmaceutical or pharmaceutical topical composition.

A topical composition according to the invention, intended to be applied to the skin or mucous membranes of man or animals, can be composed of a topical emulsion comprising at least one aqueous phase and at least one oil phase. This topical emulsion can be of the oil-in-water (O/W), water-in-oil (W/O), oil-in-water-in-oil (O/W/O) or water-in-oil-in-water (W/O/W) type. The oil phase of the topical emulsion can be composed of a mixture of one or more oils.

A topical composition according to the invention can be intended for a cosmetic use or can be used to prepare a medicament intended for the treatment of diseases of the skin, scalp and mucous membranes. In the latter case, the topical composition then comprises an active principle which can, for example, be an anti-inflammatory agent, a muscle relaxant, an antifungal, an antibacterial or an antidandruff agent.

When the topical composition is used as cosmetic composition intended to be applied to the skin, to the scalp or to the mucous membranes, it may or may not comprise an active principle, for example a moisturizing agent, a tanning agent, a sunscreen, an antiwrinkle agent, an agent having a slimming purpose, an agent for combating free radicals, an antiacne agent, an antifungal or an antidandruff agent.

The topical composition according to the invention normally comprises between 0.1% and 10% by weight and more particularly from 1% to 5% by weight of the anionic polyelectrolyte as defined above.

According to a specific aspect, the topical composition as defined above additionally comprises from 1% by weight to 10% by weight of glycerol.

The pH of the topical composition is preferably greater than or equal to 3.

The topical composition can additionally comprise compounds conventionally included in compositions of this type, for example fragrances, preservatives, dyes, pigments, sunscreens, active ingredients, emollients or surfactants.

The anionic polyelectrolyte according to the invention is an advantageous substitute for the inverse latexes sold under the names of Sepigel™ 305, Sepigel™ 501, Simulgel™ EG, Simulgel™ EPG, Simulgel™ NS, Simulgel™ INS 100, Simulgel™ 600, Simulgel™ A, Sepiplus™ 265, Sepiplus™ 250, Sepiplus™ 400 or Sepiplus™ S by the Applicant Company as it also exhibits good compatibility with the other excipients used in the preparation of formulations such as milks, lotions, creams, soaps, baths, balms, shampoos or conditioners. It can also be employed with said Sepigel™ and/or Simulgel™ and/or Sepiplus™ products.

It is in particular compatible with the concentrates described and claimed in the international publications WO 92/06778, WO 95/04592, WO 95/13863, WO 96/37285, WO 98/22207 or WO 98/47610 or in FR 2 734 496, with the surfactants described in WO 93/08204. It is particularly compatible with Montanov™ 68, Montanov™ 82, Montanov™ 202, Montanov™ L, Montanov™ S, Fluidanov™ 20X or Easynov™.

It can also be used to form aqueous gels at acidic pH which are cosmetically or physiologically acceptable, such as those described in WO 93/07856; it can also be used in combination with nonionic celluloses to form, for example, styling gels, such as those described in EP 0 684 024, or also in combination with esters of fatty acids and of sugar to form compositions for the treatment of the hair or skin, such as those described in EP 0 603 019, or also in shampoos or conditioners, such as described and claimed in WO 92/21316, or, finally, in combination with an anionic homopolymer, such as Carbopol™, to form hair treatment products, such as those described in DE 19523596.

It is also compatible with N-acylated derivatives of amino acids, which allows it to be used in soothing compositions, in particular for sensitive skin, such as those described or claimed in WO 92/21318, WO 94/27561 or WO 98/09611. It is also compatible with thickening and/or gelling polymers, such as hydrocolloids of vegetable or biosynthetic origin, for example xanthan gum, gum karaya, carrageenates, alginates or galacto-mannans; such as silicates; such as cellulose and its derivatives; such as starch and its hydrophilic derivatives; or such as polyurethanes.

The anionic polyelectrolyte according to the invention in addition makes it possible to dispense with the use of silicone oil in topical compositions comprising glycerol, in that it inhibits the sticky effect brought about by this trial.

For this reason, according to a final aspect, a subject matter of the invention is a topical composition comprising between 0.1% and 10% by weight and more particularly from 1% to 5% by weight of the anionic polyelectrolyte as defined above and from 1% by weight to 10% by weight of glycerol and characterized in that it is devoid of silicone oil.

The following examples illustrate the invention without, however, limiting it.

EXAMPLE 1

Preparation of an AA/ACR-D2 Copolymer 88.2 g of acrylic acid (AA) are charged to a reactor maintained at 25° C. with stirring and containing 270 g of ethyl acetate and 230 g of cyclohexane.

After a time sufficient to achieve good homogenization of the solution, the latter is deoxygenated by sparging with nitrogen and then 7.1 g of Silmer™ ACR D2 (compound of formula (Ib), identified under the Chemical Abstract number RN=158061-40-6, with a molecular weight equal to 1400) are added.

The reaction mixture is left stirring for sixty minutes; it is then heated until the temperature of 60° C. is reached. 0.5 g of dilauroyl peroxide is then added thereto. The reaction medium is subsequently again left stirring for approximately 60 minutes, then brought to 80° C. and left at this temperature for five hours. After cooling, the powder which has formed during polymerization is filtered off and dried in order to obtain the desired product, subsequently known as: Polyelectrolyte 1.

Evaluation of the Thickening Power

Viscosity ($\mu$) of an aqueous dispersion comprising 2% by weight of Polyelectrolyte 1, the pH being adjusted to 7 [Brookfield RVT, Spindle 6, Rate: 5 revolutions/minute (S6, R5)]: $\mu$=70 200 mPa·s.

Viscosity ($\mu$) of an aqueous dispersion comprising 1% by weight of Polyelectrolyte 1, the pH being adjusted to 7, and 1% by weight of sodium chloride [Brookfield RVT (S6, R5)]: $\mu$=7400 mPa·s.

Evaluation of the Sticky Nature of Aqueous Gels Comprising Glycerol

An aqueous gel is prepared by mixing 1.875 g of Polyelectrolyte 1, 25 g of glycerol and 223.125 g of deionized water.

As basis for comparison, an aqueous gel is prepared by mixing 4.7 g of Sepigel™ 305, 25 g of glycerol and 220.3 g of water.

On spreading each of the two gels over a different surface of the back of the hand, the absence of sticky effect is observed for the gel comprising Polyelectrolyte 1 according to the invention, contrary to the gel according to the state of the art.

EXAMPLE 2

Preparation of an AA/ACR-D2 Copolymer

The operation is carried out in the same way as in example 1 but reducing the amount of Silmer™ ACR D2 employed to 4.4 g. Polyelectrolyte 2 is obtained.

Evaluation of the Thickening Power

Viscosity ($\mu$) of an aqueous dispersion comprising 0.5% by weight of Polyelectrolyte 2, the pH being adjusted to 7 [Brookfield RVT (S6, R5)]: $\mu$=108 000 mPa·s.

Viscosity ($\mu$) of an aqueous dispersion comprising 1% by weight of Polyelectrolyte 2, the pH being adjusted to 7, and 1% by weight of sodium chloride [Brookfield RVT (S6, R5)]: $\mu$=12 000 mPa·s.

Evaluation of the Sticky Nature of Aqueous Gels Comprising Glycerol

An aqueous gel is prepared by mixing 1.875 g of Polyelectrolyte 2, 25 g of glycerol and 223.125 g of deionized water.

As basis for comparison, an aqueous gel is prepared by mixing 4.7 g of Sepigel™ 305, 25 g of glycerol and 220.3 g of water.

On spreading each of the two gels over a different surface of the back of the hand, the absence of sticky effect is observed for the gel comprising Polyelectrolyte 2 according to the invention, contrary to the gel according to the state of the art.

EXAMPLE 3

Preparation of an AA/ACR-D2 Copolymer

The operation is carried out in the same way as in example 1 but reducing the amount of Silmer™ ACR D2 employed to 2.6 g. Polyelectrolyte 3 is obtained.

Evaluation of the Thickening Power

Viscosity ($\mu$) of an aqueous dispersion comprising 0.5% by weight of Polyelectrolyte 3, the pH being adjusted to 7 [Brookfield RVT (S6, R5)]: $\mu$=39 800 mPa·s.

Viscosity ($\mu$) of an aqueous dispersion comprising 1% by weight of Polyelectrolyte 3, the pH being adjusted to 7, and 1% by weight of sodium chloride [Brookfield RVT (S6, R5)]: $\mu$=15 800 mPa·s.

Evaluation of the Sticky Nature of Aqueous Gels Comprising Glycerol

An aqueous gel is prepared by mixing 1.875 g of Polyelectrolyte 3, 25 g of glycerol and 223.125 g of deionized water.

As basis for comparison, an aqueous gel is prepared by mixing 4.7 g of Sepigel™ 305, 25 g of glycerol and 220.3 g of water.

On spreading each of the two gels over a different surface of the back of the hand, the absence of sticky effect is observed for the gel comprising Polyelectrolyte 3 according to the invention, contrary to the gel according to the state of the art.

EXAMPLE 4

Preparation of an AA/ACR-D2/SMA Copolymer

The operation is carried out in the same way as in example 3 but additionally adding 8.1 g of stearyl methacrylate. Polyelectrolyte 4 is obtained.

Evaluation of the Thickening Power

Viscosity ($\mu$) of an aqueous dispersion comprising 0.5% by weight of Polyelectrolyte 4, the ph being adjusted to 7 [Brookfield RVT (S6, R5)]: $\mu$=15 600 mPa·s.

Viscosity ($\mu$) of an aqueous dispersion comprising 1% by weight of Polyelectrolyte 4, the pH being adjusted to 7, and 1% by weight of sodium chloride [Brookfield RVT (S6, R5)]: $\mu$=13 100 mPa·s.

Evaluation of the Sticky Nature of Aqueous Gels Comprising Glycerol

An aqueous gel is prepared by mixing 1.875 g of Polyelectrolyte 4, 25 g of glycerol and 223.125 g of deionized water.

As basis for comparison, an aqueous gel is prepared by mixing 4.7 g of Sepigel™ 305, 25 g of glycerol and 220.3 g of water.

On spreading each of the two gels over a different surface of the back of the hand, the absence of sticky effect is observed for the gel comprising Polyelectrolyte 4 according to the invention, contrary to the gel according to the state of the art.

Examples of Formulations Comprising Glycerol and Devoid of Silicone Oils Prepared With Polyelectrolytes According to the Invention

EXAMPLE 5

Make-Up-Removing Emulsion Comprising Sweet Almond Oil

Montanov™ 68: 5%
Sweet almond oil: 5%
Water: q.s. for 100%
Polyelectrolyte 1: 0.3%
Glycerol: 5%
Preservative: 0.2%
Fragrance: 0.3%

EXAMPLE 6

Emulsion for Atopy-Prone Skin

Arlacel™ P135: 2.00%
Polyelectrolyte 4: 1.00%
Lanol™ 1688: 14.00%
Primol™ 352: 8.00%
Glycerol: 5.00%
Water: q.s. for 100%
Magnesium sulfate: 0.70%
Sepicide™ HB: 0.30%
Sepicide™ CI: 0.20%
Micropearl™ M310: 5.00%

The definitions of the commercial products used in the examples are as follows:

Montanov™ 68 (cetearyl glucoside) is a self-emulsifiable composition as described in WO 92/06778, sold by SEPPIC.

Arlacel™ P135 is a mixture of glycerol monostearate, glycerol distearate and polyoxyethylene glycerol stearate, sold by Croda.

Sepicide™ CI, imidazolidinyl urea, is a preservative, sold by SEPPIC.

Lanol™ 1688 is an emollient ester having a nongreasy effect, sold by SEPPIC.

Sepicide™ HB, which is a mixture of phenoxyethanol, methylparaben, ethylparaben, propylparaben and butyl-paraben, is a preservative, sold by SEPPIC.

Micropearl™ M 310 is an ultrafine powder with a very soft feel and with a mattifying action, sold by Matsumo.

Primol™ 352 is a mineral oil, sold by Exxon.

The invention claimed is:

1. A linear, branched or crosslinked anionic polyelectrolyte resulting from the polymerization, for 100% by weight:
  a) of a proportion by weight of greater than or equal to 80% and less than or equal to 99.5% of monomer units resulting from a monomer comprising a weak acid functional group;
  b) of a proportion by weight of greater than or equal to 0.5% and less than or equal to 20%,
   either of a monomer of formula (Ia):

$$R-(CH_2)_3-Si(CH_3)_2-[O-Si(CH_3)_2-]_nO-Si(CH_3)_2-(CH_2)_3-R \quad (Ia),$$

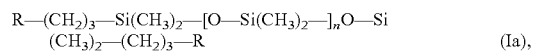

in which:
   R represents the monovalent radical:

$$-(O-CH_2-CH_2-)_x[O-CH_2-CH(CH_3)-]_yO-C(=O)-CH=CH_2,$$

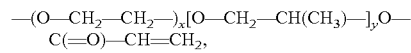

in which x and y represent, independently of one another, an integer of greater than or equal to 0 and less than or equal to 40, it being understood that the sum x+y is greater than 0 and less than 50; and
   n represents an integer of greater than or equal to 0 and less than or equal to 45,
   said monomer of formula (Ia) having a molecular weight of greater than or equal to 1500 and less than or equal to 7000;
   or of a monomer of formula (Ib):

$$Si(CH_3)_3-[O-Si(CH_3)_2-]_m[O-Si(CH_3)[(CH_2)_3-R]-]_pO-Si(CH_2)_3 \quad (Ib),$$

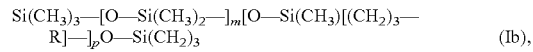

in which:
   R represents a monovalent radical of formula:

$$-(O-CH_2-CH_2-)_x[O-CH_2-CH(CH_3)-]_yO-C(=O)-CH=CH_2,$$

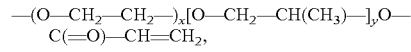

in which x and y represent, independently of one another, an integer of greater than or equal to 0 and less than or equal to 40, it being understood that the sum x+y is greater than 0 and less than 50;
   m represents an integer of greater than or equal to 1 and less than or equal to 7, and
   p represents, independently of m, an integer of greater than or equal to 1 and less than 20;
   said monomer of formula (Ib) having a molecular weight of greater than or equal to 1000 and less than or equal to 4000;
  c) optionally of a proportion by weight of greater than 0% and less than or equal to 5% of monomer units resulting from at least one monomer of formula (II):

$$R_2-C(=O)-O-[(CH_2-CH(R_4)-O]_m-R_3 \quad (II),$$

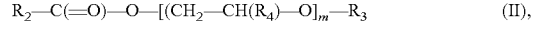

in which formula (II) m represents a number greater than or equal to 0 and less than or equal to 50, $R_2$ represents an unsaturated monovalent aliphatic radical comprising from 2 to 4 carbon atoms, $R_4$ represents a hydrogen atom, a methyl radical or an ethyl radical and $R_3$ represents a saturated or unsaturated, linear or branched, aliphatic hydrocarbon radical comprising from 8 to 30 carbon atoms, and
  d) optionally of a proportion by weight of greater than 0% and less than or equal to 5% of at least one diethylenic or polyethylenic crosslinking monomer.

2. The anionic polyelectrolyte as defined in claim 1, for which said monomer comprising a weak acid functional group is chosen from acrylic acid, methacrylic acid, itaconic acid, maleic acid or 3-methyl-3-[(1-oxo-2-propenyl)amino]butanoic acid.

3. The anionic polyelectrolyte as defined in claim 2, for which said monomer comprising a weak acid functional group is acrylic acid.

4. The anionic polyelectrolyte as defined in claim 1, for which said monomer of formula (II) is chosen from pentacosaethoxylated behenyl methacrylate, tetraethoxylated lauryl acrylate, eicosaethoxylated stearyl methacrylate, tetraethoxylated lauryl methacrylate or stearyl methacrylate.

5. The anionic polyelectrolyte as defined in claim 1 resulting from the polymerization, for 100% by weight:
 a) of a proportion by weight of greater than or equal to 85% and less than or equal to 98% of monomer units resulting from a monomer comprising a weak acid functional group;
 b) of a proportion by weight of greater than or equal to 1% and less than or equal to 14% of monomer units resulting from a monomer of formula (Ia) as defined above or from a monomer of formula (Ib) as defined above; and
 c) of a proportion by weight of greater than or equal to 1% and less than or equal to 5% of monomer units resulting from the compound of formula (II) as defined above.

6. The anionic polyelectrolyte as defined in claim 1, characterized in that it is crosslinked.

7. The anionic polyelectrolyte as defined in claim 6, characterized in that said at least one diethylenic or polyethylenic crosslinking monomer is chosen from methylenebis(acrylamide) or trimethylolpropane triacrylate.

8. A process for the preparation of the polyelectrolyte as defined in claim 1, characterized in that it comprises:
 a stage a) of preparation of a reaction mixture comprising, in the desired molar proportions and in an organic solvent (S), the monomer or monomers comprising a weak acid functional group, the monomer of formula (Ia) or the monomer of formula (Ib); if necessary or if desired, the monomer units resulting from the compound of formula (II); and, if necessary or if desired, the diethylenic or polyethylenic crosslinking monomer or monomers,
 a stage b) during which the polymerization reaction is initiated by introduction, into said reaction mixture prepared in stage a), of a free radical initiator and is then allowed to take place until its conclusion, in order to obtain a precipitate of said polyelectrolyte, if necessary or if desired,
 a stage c) of isolation of said precipitate obtained in stage b) by separation from said solvent (S) and then, if necessary or if desired,
 a stage d) of drying said precipitate resulting from stage c).

9. The process as defined in claim 8, in which the solvent (S) is a cyclohexane/ethyl acetate mixture.

10. A cosmetic, dermopharmaceutical or pharmaceutical topical composition comprising the anionic polyelectrolyte as defined in claim 1 as thickener and/or as stabilizer and/or as emulsifier.

11. A topical cosmetic composition, characterized in that it comprises from 1% to 5% by weight of the anionic polyelectrolyte as defined in claim 1 and from 1% by weight to 10% by weight of glycerol.

12. The composition as defined in claim 11, characterized in that it is devoid of silicone oil.

13. A method of preparing a cosmetic, dermopharmaceutical or pharmaceutical topical composition comprising adding to said cosmetic, dermopharmaceutical or pharmaceutical topical composition, the anionic polyelectrolyte as defined in claim 1 as thickener and/or as stabilizer and/or as emulsifier to said cosmetic, dermopharmaceutical or pharmaceutical topical composition.

* * * * *